United States Patent

Geders et al.

[11] Patent Number: 6,092,764
[45] Date of Patent: *Jul. 25, 2000

[54] INTERFACE SEAL FOR AN AIRCRAFT

[75] Inventors: Paul Francis Geders, Florissant; Robert Henry Wille, St. Charles, both of Mo.

[73] Assignee: McDonnell Douglas Corporation, Huntington Beach, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/897,341

[22] Filed: Jul. 21, 1997

[51] Int. Cl.⁷ ...................................................... B64C 1/00
[52] U.S. Cl. ...................... 244/117 R; 244/130; 244/131
[58] Field of Search ..................................... 244/130, 131, 244/49, 117 R, 123; 16/225; 277/634, 637

[56] References Cited

U.S. PATENT DOCUMENTS

| | | |
|---|---|---|
| 2,368,702 | 2/1945 | Bourne . |
| 2,731,221 | 1/1956 | Holton . |
| 3,029,480 | 4/1962 | Signorelli et al. ...................... 244/131 |
| 3,499,622 | 3/1970 | Lugan et al. ............................. 244/130 |
| 4,387,903 | 6/1983 | Smith ...................................... 277/634 |
| 4,427,169 | 1/1984 | Brown ..................................... 244/130 |
| 4,429,844 | 2/1984 | Brown et al. ............................ 244/219 |
| 4,485,993 | 12/1984 | Mueller ................................... 244/130 |
| 4,892,626 | 1/1990 | Covey . |
| 5,222,699 | 6/1993 | Albach et al. ........................... 244/213 |
| 5,552,576 | 9/1996 | Giamati ................................. 244/129.1 |
| 5,662,294 | 9/1997 | Maclean et al. . |
| 5,794,893 | 8/1998 | Diller et al. ............................. 244/130 |
| 5,803,405 | 9/1998 | Ellis et al. ............................... 244/130 |
| 5,810,291 | 9/1998 | Geiger et al. ............................. 16/224 |
| 5,845,877 | 12/1998 | Justice et al. ........................... 244/131 |
| 5,896,191 | 4/1999 | Beier et al. . |
| 5,927,651 | 7/1999 | Geders et al. . |
| 5,947,417 | 9/1999 | Cameron . |
| 5,947,422 | 9/1999 | Wille . |
| 5,988,567 | 11/1999 | Wille . |

OTHER PUBLICATIONS

U. S. Ser. No. 08/932,947; filed 9/17/97; (allowed).
U.S. Ser. No. 09/082,817; filed 5/21/98; (pending).
U.S. Ser. No. 09/108,858; filed 7/1/98; (pending).
U.S. Ser. No. 08/898,162; filed 7/22/97; (allowed).
U.S. Ser. No. 08.897,341; filed 7/21/97; (pending).
U.S. Ser. No. 08/576,298; filed 12/21/95; (allowed).
U.S. Ser. No. 08/718,771; filed 9/24/96; (adandoned).
U.S. Ser. No. 08/718,771; filed 8/20/98; (pending).
U.S. Ser. No. 08/814,497; filed 3/10/97; (pending).
U.S. Ser. No. 09/094,299; filed 6/9/98; (pending).
U.S. Ser. No. 08/576,466; filed 12/21/95; (allowed).
U.S. Ser. No. 08/807,295; filed 2/27/97; (allowed).
U.S. Ser. No. 09/294,443; filed 8/17/98; (pending).
U.S. Ser. No. 09/294,444; filed 8/17/98; (pending).
U.S. Ser. No. 08/818,108; filed 3/13/97; issued as U.S. Patent No. 5,958,803;
U.S. Ser. No. 08/848,228; filed 4/30/97; (pending).

*Primary Examiner*—Galen L. Barefoot
*Attorney, Agent, or Firm*—Harness Dickey & Pierce P.L.C.

[57] ABSTRACT

An interface seal (52) for an aircraft (50) has a first rigid structural beam (60) attached to a first portion of the aircraft (50). A second rigid structural beam (64) is attached to a second portion of the aircraft (50). An elastomer skin (62) is connected to the first rigid structural beam (60) and attached to the second rigid structural beam (64).

12 Claims, 3 Drawing Sheets

INTERFACE SEAL FOR AN AIRCRAFT

FIELD OF THE INVENTION

The present invention relates generally to the field of aircraft and more particularly to an interface seal for an aircraft.

BACKGROUND OF THE INVENTION

Modern aircraft place tremendous loads, that vary quickly, on their wings. These loads result in structural deformation of the wings and fuselage of the aircraft that create gaps between components near the wing-fuselage interface. Dirt and objects can become lodged inside these gaps. In addition, electromagnetic interference (EMI) can enter the aircraft through these gaps. Present seals use overlapping rigid plates to cover the gap. Unfortunately, the doubly-curved moldlines of aircraft in these areas present a very difficult arrangement for overlapping seals to be effective and significant space must be left between the plates. This provides a passage way for dirt, objects and EMI. Thus there exists a need for a seal that can accommodate the structural deformations between the wings (or a tail, or a control surface) and the fuselage, without leaving a passage way for dirt, objects or EMI.

SUMMARY OF THE INVENTION

An interface seal for an aircraft, that overcomes these and other problems has a first rigid structural beam attached to a first portion of the aircraft. A second rigid structural beam is attached to a second portion of the aircraft. An elastomer panel is connected to the first rigid structural beam and attached to the second rigid structural beam.

DETAILED DESCRIPTION OF THE DRAWINGS

Figure 1:
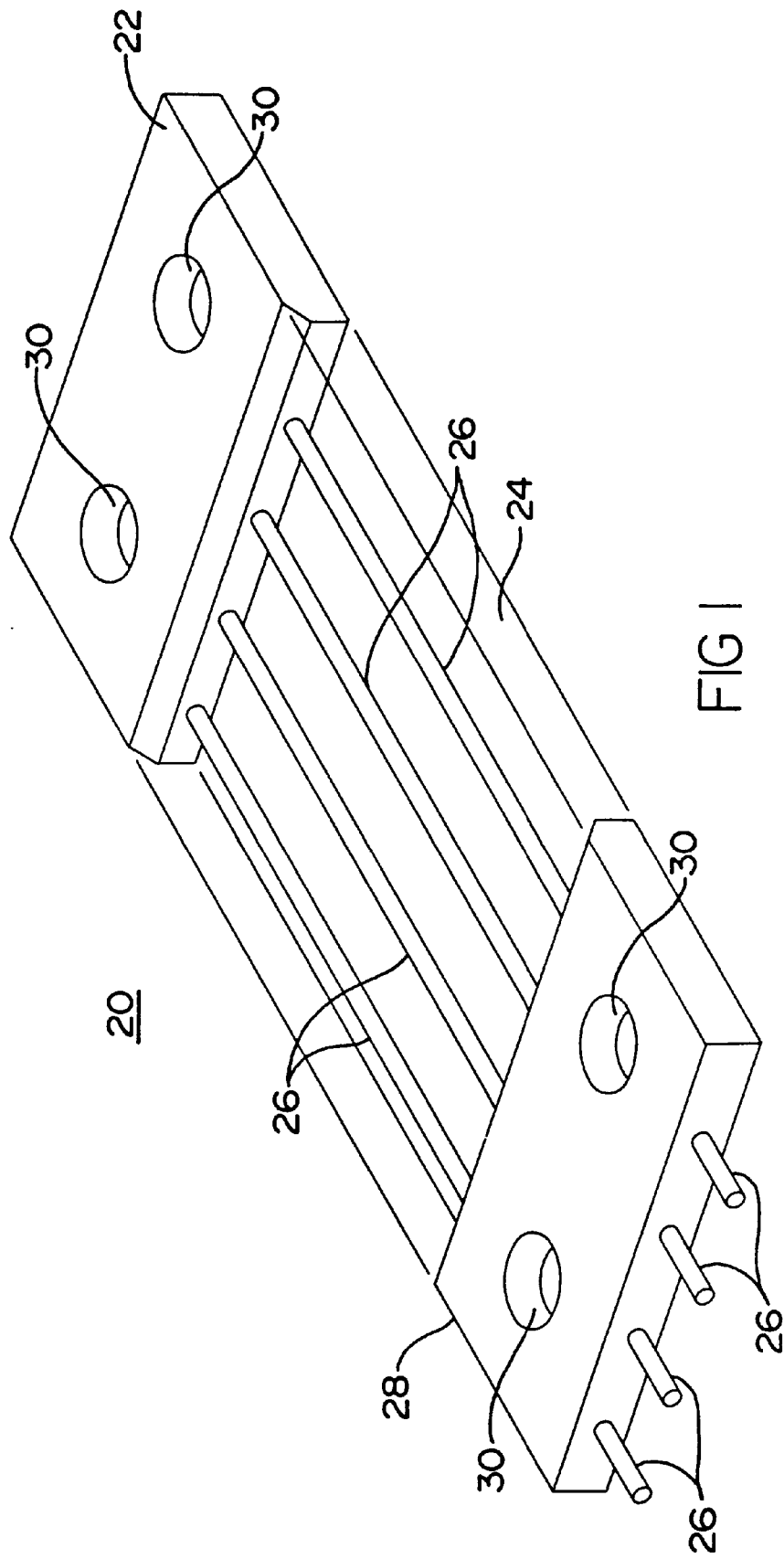
FIG. 1 is a perspective view of a reinforced elastomer panel.

The key to building a seal for an aircraft that does not have a passage way for dirt, objects and EMI is designing a seal that takes advantage of a modified version of the reinforced elastomer panel shown in FIG. 1. The elastomer panel 20 has a rod block 22 attached along one edge to an elastomer skin 24. The elastomer skin 24 is capable of stretching to 100% of its unstressed length. In addition, the elastomer skin 24 is capable of twisting. A plurality of rods 26 are attached to the rod block 22 and are allowed to slide freely inside the elastomer skin 24. The rods 26 are made from quartz, epoxy or composites and flex without breaking. The stiffness of these reinforcements are designed to yield a specific expanded shape. The rods 26 provide the elastomer skin 24 with a curvilinear shape when the elastomer panel 20 is elongated, deflected or twisted. This curvilinear shape provides a good aerodynamic shape without any discontinuities that cause turbulence and drag.

A second rod block 28 is attached to an opposite edge of the elastomer skin 24. The second rod block 28 has a plurality of holes through which the plurality of rods 26 are allowed to slide freely. Both the rod block 22 and the second rod block 28 have attachment provisions 30, for attaching the elastomer panel 20 to the surface of an aircraft.

Figure 2:
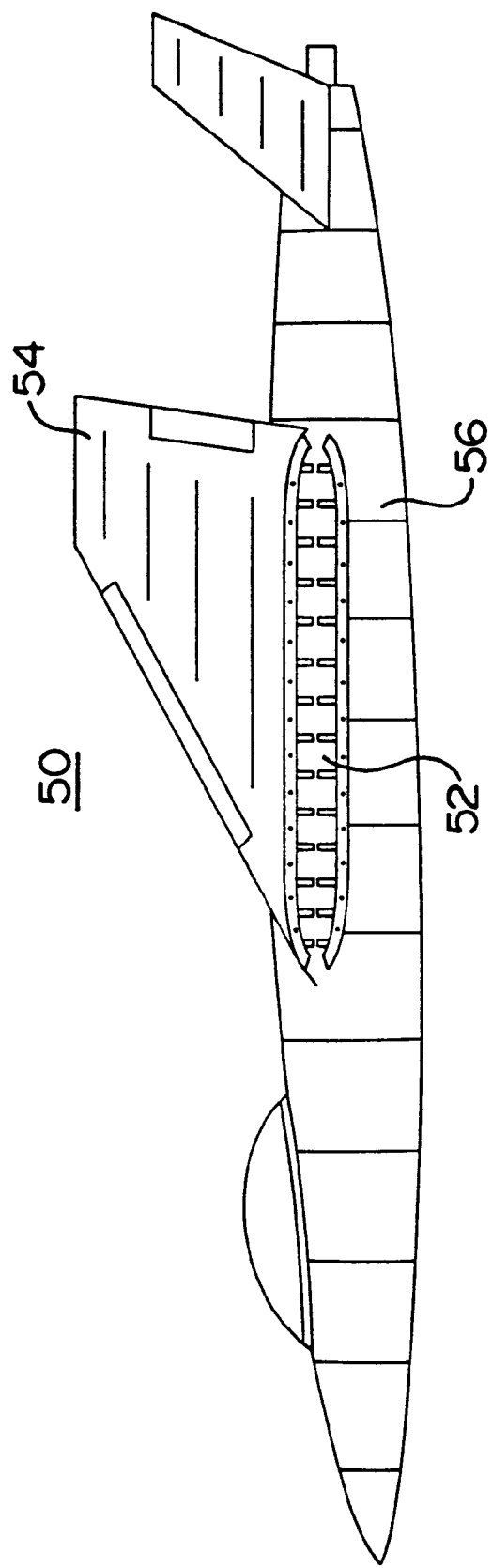
FIG. 2 is a perspective view of an aircraft.
Figure 3:
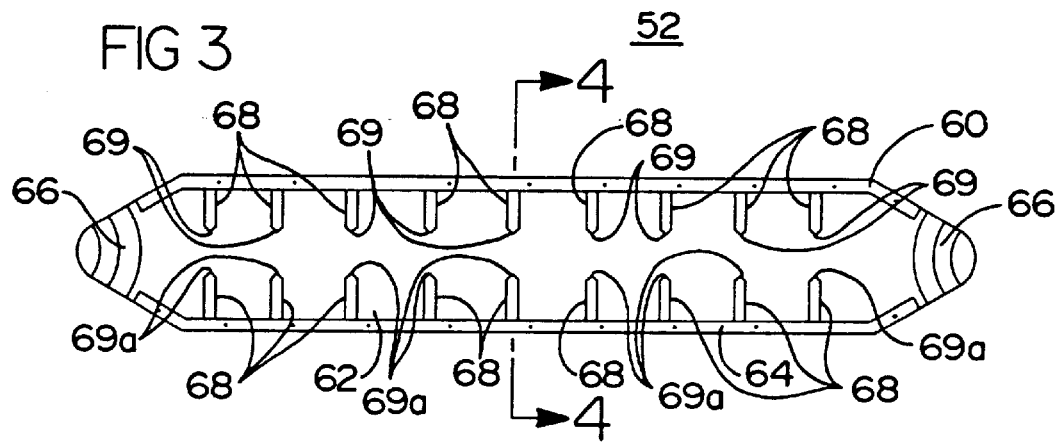
FIG. 3 is a top view of an embodiment of seal for an aircraft.
Figure 4:
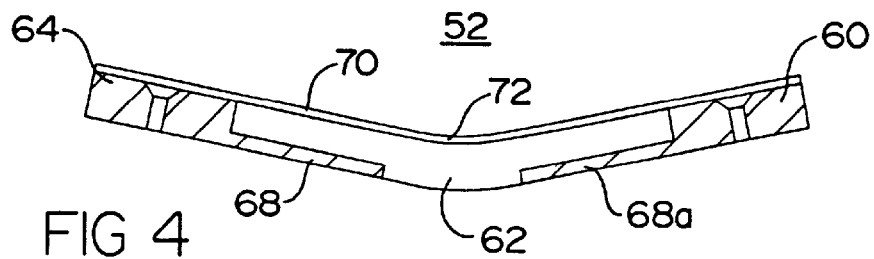
FIG. 4 is a cross sectional view of the seal of FIG. 3 taken along the A—A line.
Figure 5:
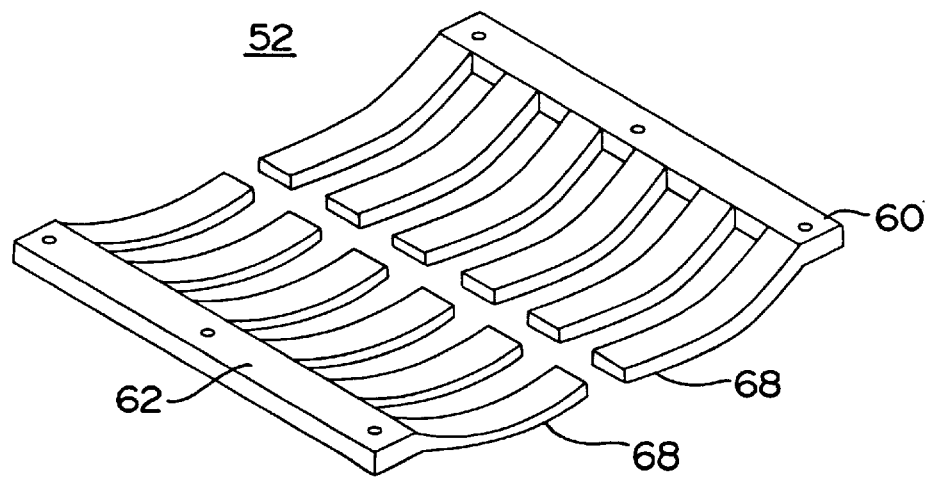
FIG. 5 is a partial perspective view of the seal of FIG. 3.

FIG. 2 is a perspective view of an aircraft 50 having a seal 52 between a wing 54 and a fuselage 56 of the aircraft 50. The seal 52, in one embodiment, is a modified version of the reinforced elastomer panel 20 of FIG. 1. As shown in FIG. 3, the seal 52 has a first rigid structural beam 60 attached to an elastomer skin 62. The first rigid structural beam 60 is attached to the wing of the aircraft. A second rigid structural beam 64 is attached to the elastomer skin 62 and attached by screws for instance to the fuselage of the aircraft. The seal 52 has a pair of fairings 66 at each end of the seal 52. The fairings 66, shown in FIG. 3 are made of elastomer and the rigid structural beams 60, 64 terminate in the fairings. The first rigid structural beam 60 having a first end terminating at the first fairing 66 and a second end terminating at the second fairing 66. The second rigid structural beam 64 having a first end terminating at the first fairing 66 and a second end terminating at the second faring 66. The structural beams 60, 64 are shown in FIG. 4. A plurality of composite fingers (structural beams) 68 extend from the rigid structural beams 60, 64 into the elastomer skin 62. Note that the first plurality of composite fingers 68 attached to the first structural beam 60 each have a first tip 69 and the second plurality of composite fingers 68 attached to the second structural beqm 68 each have a second tip 69a, the, first tip 69 separated by a distance from the second tip 69a. The composite fingers 68 provide a stiffness to the elastomer skin 62 and provide a smooth curvilinear surface as the seal 52 expands and contracts. In one embodiment the seal is covered with a conductive layer covering 70. In another embodiment an environmental coating cover 72 is placed over the conductive layer covering 70 or directly over the seal.

The conductive layer covering 70 provides an electromagnetic interference (EMI) seal that prevents EMI from entering the aircraft and damaging sensitive electronic equipment. The conductive layer covering 70 in one embodiment is a stretchable fabric coated with metal and encased in elastomer.

The environmental coating 72 protects the seal from jet fuel, grease and other solvents. The environmental coating in one embodiment is made from fluorosilicones, fluoroelastomers, silicones, thermoplastic elastomers, urethanes or other viable elastic materials.

The seal 52 can expand a contract as the wing and fuselage are forced together and apart by the aerodynamic forces. As a result the seal prevents dirt, objects and EMI from entering between the wing (other control surface) and the fuselage of the aircraft.

Thus there has been described a seal for an aircraft that prevents dirt, objects and EMI from entering the aircraft between the wing and the fuselage. While the invention has been described in conjunction with specific embodiments thereof, it is evident that many alterations, modifications, and variations will be apparent to those skilled in the art in light of the foregoing description. Accordingly, it is intended to embrace all such alterations, modifications, and variations in the appended claims.

What is claimed is:

1. An interface seal for an aircraft, comprising:

a first rigid structural beam attached to a first portion of the aircraft;

a second rigid structural beam attached to a second portion of the aircraft;

an elastomer skin connected to the first rigid structural beam and attached to the second rigid structural beam;

a first plurality of composite fingers integrally formed with the first rigid structural beam and extending into the elastomer skin;

a second plurality of composite fingers integrally formed with the second rigid structural beam and extending into the elastomer skin generally towards the first plurality of composite fingers; and wherein the first plurality of composite fingers each have a first tip and the second plurality of composite fingers each have a second tips, the first tips separated by a distance from the second tips to thereby provide a gap between the first and second pluralities of composite fingers within the elastomer skin.

2. The interface seal of claim 1, wherein the first plurality of composite fingers and the second plurality of composite fingers extend in general longitudinal alignment with one another.

3. The interface seal of claim 1, wherein the first plurality of composite fingers are at least substantially enveloped by the elastomer panel.

4. The interface seal of claim 1, further including a first fairing attached to an end of the first rigid structural beam.

5. The interface seal of claim 4, wherein the first fairing is made of an elastomer.

6. The interface seal of claim 1, further including a conductive fabric covering the elastomer skin.

7. The interface seal of claim 1, wherein the first portion of the aircraft is a wing and the second portion of the aircraft is a fuselage.

8. An interface seal for an aircraft, comprising:

an elastomer sheet having a first long edge connected to a first portion of the aircraft, and a second long edge connected to a second portion of the aircraft;

a first fairing connected to a first short edge of the elastomer sheet;

a second fairing connected to a second short edge of the elastomer sheet;

a first structural beam attached along the first long edge of the elastomer sheet, the first structural beam including a first plurality of composite fingers, the first structural beam having a first end terminating at the first fairing and a second end terminating at the second fairing; and a second structural beam attached along the second long edge of the elastomer sheet, the second structural beam including a second plurality of composite fingers, the second structural beam having a first end terminating at the first fairing and a second end terminating at the second fairing.

9. The interface seal of claim 8, further including a conductive layer covering the elastomer sheet.

10. The interface seal of claim 9, further including an environmental coating covering the elastomer sheet.

11. A seal for an aircraft, comprising:

a first fairing;

a second fairing a first rigid structural beam having a first end terminating at the first fairing and a second end terminating at the second fairing, the first rigid structural beam attached to a first portion of the aircraft;

a second rigid structural beam having a first end terminating at the first fairing and a second end terminating at the second fairing, the second rigid structural beam attached to a second portion of the aircraft;

an elastomer skin connected to the first rigid structural beam and attached to the second rigid structural beam;

a first plurality of composite fingers attached to the first rigid structural beam and extending into the elastomer skin;

a second plurality of composite fingers attached to the second rigid structural beam and extending into the elastomer skin; and wherein the first plurality of composite fingers each have a first tip and the second plurality of composite fingers each have a second tip, the first tip separated by a distance from the second tip.

12. The seal of claim 11, wherein the second fairing is made of an elastomer.

* * * * *